(12) United States Patent
Essers et al.

(10) Patent No.: US 8,420,886 B2
(45) Date of Patent: Apr. 16, 2013

(54) TRANSGENIC MOUSE COMPRISING A DISRUPTED FIBULIN-4 GENE AS A MODEL FOR CARDIOVASCULAR DISEASE

(75) Inventors: Jeroen Essers, Rotterdam (NL); Georgios Aris Garinis, Crete (GR); Roland Kanaar, Rotterdam (NL)

(73) Assignee: Erasmus University Medical Center Rotterdam, Rotterdam (NL)

( * ) Notice: Subject to any disclaimer, the term of this patent is extended or adjusted under 35 U.S.C. 154(b) by 749 days.

(21) Appl. No.: 11/996,392

(22) PCT Filed: Jul. 22, 2005

(86) PCT No.: PCT/NL2005/000532
§ 371 (c)(1),
(2), (4) Date: Jul. 19, 2010

(87) PCT Pub. No.: WO2007/011202
PCT Pub. Date: Jan. 25, 2007

(65) Prior Publication Data
US 2011/0083199 A1    Apr. 7, 2011

(51) Int. Cl.
*A01K 67/027* (2006.01)
*G01N 33/00* (2006.01)

(52) U.S. Cl.
USPC .................................. 800/18; 800/3; 800/25

(58) Field of Classification Search .................. None
See application file for complete search history.

(56) References Cited

U.S. PATENT DOCUMENTS
2005/0119536 A1* 6/2005 Hageman ...................... 600/300

FOREIGN PATENT DOCUMENTS
| EP | 1241187 A2 | 9/2002 |
| WO | 02072138 A1 | 9/2002 |
| WO | 2004063225 A2 | 7/2004 |
| WO | 2005083126 A2 | 9/2005 |

OTHER PUBLICATIONS

Argraves et al. Fibulins: physiological and disease perspectives. EMBO Reports, 2003, vol. 4, pp. 1127-1131.*
Prelle et al. Establishment of Pluripotent Cell Lines from Vertebrate Species—Present Status and Future Prospects. Cell Tissues Organs, 1999, vol. 165, pp. 220-236.*
Moreadith. Gene targeting in embryonic stem cells: the new physiology and metabolism. J. Mol. Med., 1997, vol. 75 pp. 208-216).*
Denning et al. New frontiers in gene targeting and cloning: success, application and challenges in domestic animals and human embryonic stem cells. Reproduction, 2003, vol. 126, pp. 1-11.*
Smith. Gene transfer in higher animals: theoretical considerations and key concepts. Journal of Biotechnology, 2002, vol. 99, pp. 1-22.*
Nature. The Renaissance Art. Nature, 2004, vol. 428, pp. 464-466.*
Smits et al. Rat Genetics: the Next Episode. Trends in Genetics, 2006, vol. 22, pp. 232-240.*
Kostka et al. Perinatal Lethality and Endothelial Cell Abnormalities in Several Vessel Compartments of Fibulin-1-Deficient Mice. Molec. Cell. Biol., 2001, vol. 21, pp. 7025-7034.*
Chu et al., "Fibullins in Development and Heritable Disease," Birth Defects Research (Part C), 72:25-36, 2004.
Gallagher et al., "Human fibulin-4: analysis of its biosynthetic processing and mRNA expression in normal and tumour tissues," FEBS Letters, 489:59-66, 2001, Elsevier Science B.V.
Giltay et al., "Sequence, recombinant expression and tissue localization of two novel extracellular matrix proteins, fibulin-3 and fibulin-4," Matrix Biology 18:469-480, 1999, Elsevier Science B.V./International Society of Matrix Biology.
Argraves et al., "Fibulins: physiological and disease perspectives," EMBO Reports, 4(12):1127-1131, 2003, European Molecular Biology Organization.

* cited by examiner

Primary Examiner — Deborah Crouch
(74) Attorney, Agent, or Firm — The Webb Law Firm (57) ABSTRACT

The invention relates to an animal model of cardiovascular disease and a method of preparation and use thereof. In particular, it relates to a genetically engineered animal model of aortic aneurysms and methods for screening drugs using the animal model. Provided is a genetically-modified, non-human mammal, wherein the modification results in a disrupted Fibulin-4 gene. Also provided is a genetically-modified animal cell containing a disrupted Fibulin-4 gene. The mammal or animal cell can be used as a model for a cardiovascular condition or disease, preferably aortic aneurysm, more preferably thoracic aortic aneurysm. Furthermore, methods for identify or validating a compound that can be used to treat or to prevent an aberrant cardiovascular condition are provided, as well as method to identify a gene involved in the response to aortic failure.

13 Claims, 6 Drawing Sheets

| CODE | Title | Gene Symbol | Fibulin$^{R/R}$/WT | p-value |
|---|---|---|---|---|
| cell adhesion and extracellular matrix | | | | |
| 1424027_at | paxillin | Pxn | 1.3 | 0.0046 |
| 1450757_at | cadherin 11 | Cdh11 | 1.33 | 0.0031 |
| 1437148_at | actin related protein 2/3 complex, subunit 2 | Arpc2 | 1.34 | 0.0094 |
| 1438170_x_at | adhesion regulating molecule 1 | Adrm1 | 1.36 | 0.0028 |
| 1415797_at | discoidin domain receptor family, member 1 | Ddr1 | 1.37 | 0.0008 |
| 1422514_at | AE binding protein 1 | Aebp1 | 1.38 | 0.0090 |
| 1422437_at | procollagen, type V, alpha 2 | Col5a2 | 1.4 | 0.0022 |
| 1456133_x_at | integrin beta 5 | Itgb5 | 1.5 | 0.0033 |
| 1434740_at | scavenger receptor class F, member 2 | Scarf2 | 1.5 | 0.0002 |
| 1421814_at | moesin | Msn | 1.51 | 0.0067 |
| 1416700_at | ras homolog gene family, member E | Arhe | 1.55 | 0.0098 |
| 1426642_at | fibronectin 1 | Fn1 | 1.63 | 0.0012 |
| 1434089_at | synaptopodin | Synpo | 1.65 | 0.0006 |
| 1433857_at | fat tumor suppressor homolog (Drosophila) | Fath | 1.78 | 0.0025 |
| 1450199_a_at | stabilin 1 | Stab1 | 1.8 | 0.0028 |
| 1450027_at | syndecan 3 | Sdc3 | 1.82 | 0.0011 |
| 1417654_at | syndecan 4 | Sdc4 | 1.85 | 0.0077 |
| 1431320_a_at | myosin Va | Myo5a | 1.89 | 0.0059 |
| 1415944_at | syndecan 1 | Sdc1 | 1.93 | 0.0017 |
| 1422977_at | glycoprotein Ib, beta polypeptide | Gp1bb | 2.17 | 0.0063 |
| 1418599_at | procollagen, type XI, alpha 1 | Col11a1 | 2.5 | 0.0034 |
| 1418440_at | procollagen, type VIII, alpha 1 | Col8a1 | 2.62 | 0.0017 |
| 1455627_at | procollagen, type VIII, alpha 1 | Col8a1 | 3.65 | 0.0000 |
| 1427489_at | integrin alpha 8 | Itga8 | -2.26 | 0.0060 |
| 1421254_a_at | sarcoglycan gamma | Sgcg | -1.96 | 0.0001 |
| 1422340_a_at | actin, gamma 2, smooth muscle, enteric | Actg2 | -1.68 | 0.0026 |
| 1421276_a_at | dystonin | Dst | -1.48 | 0.0003 |
| 1450437_a_at | neural cell adhesion molecule 1 | Ncam1 | -1.41 | 0.0054 |

Figure 5B

| | | | | |
|---|---|---|---|---|
| Blood pressure and coagulation | | | | |
| 1417018_at | fibulin-like extracellular matrix protein 2 | Efemp2 | -3.29 | 0.0090 |
| 1437347_at | endothelin receptor type B | Ednrb | 1.2 | 0.0074 |
| 1460596_at | angiotensin II, type I receptor-associated protein | Agtrap | 1.41 | 0.0030 |
| 1420664_s_at | protein C receptor, endothelial | Procr | 1.43 | 0.0073 |
| 1416255_at | gap junction membrane channel protein alpha 4 | Gja4 | 1.48 | 0.0006 |
| 1436448_a_at | prostaglandin-endoperoxide synthase 1 | Ptgs1 | 1.59 | 0.0033 |
| 1422977_at | glycoprotein Ib, beta polypeptide | Gp1bb | 2.17 | 0.0063 |
| Apoptosis and cell death | | | | |
| 1460259_s_at | chloride channel calcium activated 2 | Clca2 | 2.47 | 0.0096 |
| 1421148_a_at | Cytotoxic granule-associated RNA binding protein-like 1 | Tial1 | 1.25 | 0.0074 |
| 1421236_at | receptor (TNFRSF)-interacting serine-threonine kinase 2 | Ripk2 | 1.27 | 0.0034 |
| 1452020_a_at | Cd27 binding protein (Hindu God of destruction) | Siva-pending | 1.29 | 0.0030 |
| 1450731_s_at | tumor necrosis factor receptor superfamily, member 21 | Tnfrsf21 | 1.3 | 0.0050 |
| 1416583_at | Bcl-associated death promoter | Bad | 1.34 | 0.0077 |
| 1417039_a_at | RIKEN cDNA 2510004L20 gene | 2510004L20Rik | 1.34 | 0.0017 |
| 1456381_x_at | myeloid cell leukemia sequence 1 | Mcl1 | 1.35 | 0.0054 |
| 1422490_at | BCL2/adenovirus E1B 19kDa-interacting protein 1 | Bnip2 | 1.4 | 0.0024 |
| 1416435_at | lymphotoxin B receptor | Ltbr | 1.43 | 0.0094 |
| 1417040_a_at | Bcl-2-related ovarian killer protein | Bok | 1.46 | 0.0032 |
| 1436319_at | sulfatase 1 | Sulf1 | 1.5 | 0.0016 |
| 1438200_at | sulfatase 1 | Sulf1 | 1.63 | 0.0002 |
| 1452622_a_at | TNFRSF1A-associated via death domain | Tradd | 1.69 | 0.0022 |
| 1437458_x_at | clusterin | Clu | 2.29 | 0.0034 |
| Replication | | | | |
| 1426652_at | minichromosome maintenance deficient 3 (S. cerevisiae) | Mcm3 | 1.53 | 0.0076 |
| 1416214_at | minichromosome maintenance deficient 4 (S. cerevisiae) | Mcm4 | 1.29 | 0.0095 |
| 1419270_a_at | deoxyuridine triphosphatase | Dutp | 1.6 | 0.0032 |

SEQUENCE LISTING

<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: Primer Efemp2

<400> SEQUENCE: 1
gggttatttg tgtctgcctc g                                              21

<210> SEQ ID NO 2
<211> LENGTH: 20
<212> TYPE: DNA
<213> ORGANISM: Artificial Sequence
<220> FEATURE:
<223> OTHER INFORMATION: Primer Efemp 2

<400> SEQUENCE: 2
tggtaggagc caggaaggtt                                                20

<210> SEQ ID NO 3
<211> LENGTH: 19
<212> TYPE: DNA
<213> ORGANISM: Artificial Sequence
<220> FEATURE:
<223> OTHER INFORMATION: Primer Mus81

<400> SEQUENCE: 3
caaagccttc cacaaaccc                                                 19

<210> SEQ ID NO 4
<211> LENGTH: 20
<212> TYPE: DNA
<213> ORGANISM: Artificial Sequence
<220> FEATURE:
<223> OTHER INFORMATION: Primer Mus81

<400> SEQUENCE: 4
tcataagcag ccaggagact                                                20

<210> SEQ ID NO 5
<211> LENGTH: 21
<212> TYPE: DNA
<213> ORGANISM: Artificial Sequence
<220> FEATURE:
<223> OTHER INFORMATION: Primer Cfl1

<400> SEQUENCE: 5
ccagaagaag tgaagaaacg c                                              21

<210> SEQ ID NO 6
<211> LENGTH: 20

```
<212> TYPE: DNA
<213> ORGANISM: Artificial Sequence
<220> FEATURE:
<223> OTHER INFORMATION: Primer Cf11

<400> SEQUENCE: 6
gaagatgaac accaggtcct                                                    20
```

TRANSGENIC MOUSE COMPRISING A DISRUPTED FIBULIN-4 GENE AS A MODEL FOR CARDIOVASCULAR DISEASE

BACKGROUND OF THE INVENTION

1) Field of the Invention

The invention relates to an animal model of cardiovascular disease and a method of preparation and use thereof. Inter alia, it relates to a genetically engineered animal model of aortic aneurysms and methods for screening drugs using the animal model.

2) Description of Related Art

The aorta, the largest artery in the body, is responsible for pumping blood out of the heart and into the organs of the body. The aorta projects upward from the heart through the chest (thoracic aorta), and then arches downward into the abdomen (abdominal aorta). By definition, an aneurysm is a permanent dilation of the arterial wall. An aortic aneurysm is a widening, bulge, or ballooning out of a portion of the aorta, usually a weak spot in the aortic wall, typically causing the vessel to progressively expand to at least 1.5 times beyond its normal diameter of one inch.

Aortic aneurysms are commonly classified according to their anatomical location. While thoracic aortic aneurysms (TAAs) involve the ascending aorta, arch or descending aorta; abdominal aortic aneurysms (AAAs) affect the part of the aorta in the abdominal cavity. A third type involves thoracoabdominal aneurysms that originate in the descending aorta and extend to the abdominal aorta.

With gradual enlargement, the aneurysm can lead to either dissection or rupture of the aorta. Dissection is when the blood enters the wall of the aorta and splits it in two. Ninety-five percent of aortic dissections originate either within the ascending or descending aorta and fewer than 5% originate in the abdominal aorta or aortic arch. Aortic dissection is caused by a deterioration of the inner lining of the aorta. There are a number of conditions that predispose a person to develop defects of the inner lining, including high blood pressure (hypertension), Marfan's disease, Ehlers-Danlos syndrome, connective tissue diseases, and defects of heart development which begin during fetal development. A dissection can also occur accidentally following insertion of a catheter, trauma, or surgery.

Depending on the nature and extent of the dissection, death can occur within a few hours of the start of a dissection. Approximately 75% of untreated people die within two weeks of the start of a dissection. Of those who are treated, 40% survive more than 10 years. Patients are usually given long term treatment with drugs to reduce their blood pressure, even if they have had surgery.

A major problem in the management of aortic aneurysms is that the symptoms of an aortic aneurysm often do not surface until the aneurysm is quite large. However, once enlarged, the aneurysm can cause the aorta to put pressure on the surrounding organs in the chest. Clinical features may include upper back pain, coughing and wheezing, hoarse voice, difficulty swallowing, swelling (edema) in the neck or arms and Horner's syndrome (constricted pupil, drooping eyelid and dry skin on one side of the face).

Clearly, a timely diagnosis can result in early intervention and dramatic improvement in the chances for survival. However, there is no screening routine for aortic aneurysms and the mechanism(s) underlying aortic aneurysm formation are poorly understood.

Mouse models of abdominal aortic aneurysms (AAAs) have been developed that use a diverse array of methods for producing the disease, including genetic manipulation and chemical induction (see for a review Daugherty et al. Arterioscler. Thromb Vasc Biol. 2004 March; 24(3):429-34). The models recapitulate some facets of the human disease including medial degeneration, inflammation, thrombus formation, and rupture. Most of the mouse models of AAA are evoked either by genetically defined approaches or by chemical means. The genetic approaches are spontaneous and engineered mutations. These include defects in extracellular matrix maturation, increased degradation of elastin and collagen, aberrant cholesterol homeostasis, and enhanced production of angiotensin peptides. The chemical approaches include the intraluminal infusion of elastase, periaortic incubations of calcium chloride, and subcutaneous infusion of AngII.

An experimental murine model for thoracic aortic aneurysms (TAAs) is also described before. Ikonomidis et al. (J. Surg. Res. 2003; 115:157-63) report a model system for chemically evoked TAA in a murine system. It was found that abluminal application of $CaCl_2$ to the thoracic aorta via left thoracotomy produces dilation, wall-thinning and disruption of mural architecture. In a related study, it was found that deletion of the TIMP-1 gene results in increased and continued progression of aneurysm formation (Ikonomidis et al. Circulation, 2004; 110(11 Suppl. 1): II1268-73).

A major drawback of the known "chemical" animal models for aneurysms is that they exhibit a large degree of variability with respect to the onset and severity of the aneurysm evoked. It appears difficult to adjust the correct dose of chemical to each individual animal, in particular when using small animals like rats and mice.

SUMMARY OF THE INVENTION

It is an object of the present invention to provide an animal model for cardiovascular conditions which could provide insight into potential mechanisms in the development and treatment of disease. In particular, it is an object to provide a reliable animal model for aortic aneurysm, which is reliable and does not require any experimental (e.g. surgical and/or chemical) treatment to evoke an aneurysm to develop or occur.

BRIEF DESCRIPTION OF THE DRAWINGS

FIG. 5. The transcriptional response of genes clustered by biological process, i.e. genes associated with adhesion and extracellular matrix, blood pressure and coagulation, apoptosis and cell cycle regulation. Indicated are the average relative expression changes of each gene in the aorta of Fibulin$^{R/R}$ mice as compared to wt littermate controls.

DETAILED DESCRIPTION OF THE INVENTION

The goals of the present invention are met by the provision of a transgenic animal model with a decreased expression of the protein Fibulin-4. The present inventors generated mice with decreased Fibulin-4 expression through transcriptional interference by targeted integration of selectable marker. It was found that reduction of Fibulin-4 expression in mice results in heart defects, aortic insufficiency and aortic dissection. The invention therefore relates to a genetically-modified, non-human mammal, wherein the modification results in a disrupted Fibulin-4 gene. Such a mammal is advantageously used as an animal model for cardiovascular disease, in particular aortic aneurysms. A basic premise of animal models of disease is that they mimic the cellular and biochemical characteristics in the progression of the human disease. An animal model provided herein can provide information on the sequence of events that culminate in the initiation, maturation and eventual rupture of human aortic aneurysms. In contrast to the known animal models for aneurysms, an animal with reduced expression of the Fibulin-4/EFEMP2 gene as disclosed herein spontaneously develops cardiovascular defects, including aneurysms, up to aortic dissection, and therefore does not require any further experimental manipulation.

A non-human mammal or an animal that is "genetically-modified" is heterozygous or homozygous for a modification that is introduced into the non-human mammal or animal cell, or into a progenitor non-human mammal or animal cell, by genetic engineering.

Fibulin-4 is also known as EGF-containing fibulin-like extracellular matrix protein 2 precursor (EFEMP2), 0610011K11Rik, Fbln4, FIBL-4, Mutant p53 binding protein 1 (MBP1), UPH1 or H411.

As is disclosed herein, Fibulin-4 heterozygous and homozygous mice are viable, born at Mendelian frequencies and appeared indistinguishable from wild-type littermates during the first two weeks. Micro-array analysis of RNA isolated from aortic tissue showed that Fibulin-4 heterozygous mice have a 2-fold reduction in Fibulin-4 RNA expression levels. Fibulin-4 heterozygous mice show slight abnormalities in the elastic fiber network of the aorta after elastin staining of cross sections of the ascending aorta but no increased mortality or abnormal appearance during the first year was observed in these mice.

However, the heterozygous animals may develop cardiovascular conditions at a later stage of life. Furthermore, they can be useful in various types of (long-term) drug studies. Accordingly, in one embodiment the animal has at least a 2-fold reduction in Fibulin-4 RNA expression levels in aortic tissue.

In a preferred embodiment, the animal is homozygous for inactivation of the fibulin-4 gene. In contrast to the relatively mild phenotype of the heterozygous mice, more than 80% of the homozygously targeted Fibulin-4 mice suddenly died after 2 weeks. Pathological analysis revealed that these mice died from aortic dissection resulting from severe abnormalities in the elastic fiber network of the aorta (elastin). Pathological analysis of heart and aorta of 10-20 week old surviving homozygous Fibulin-4 mice and determination of hemodynamic parameters showed multiple heart and aortic defects, including a 2-fold dilatation of the left ventricle and aorta, increased pulse pressure and aortic insufficiency. Thus, both the Fibulin-4 heterozygous and homozygous mice provide a unique animal model to follow the pathogenetic sequence for aneurysm.

Figure 1:
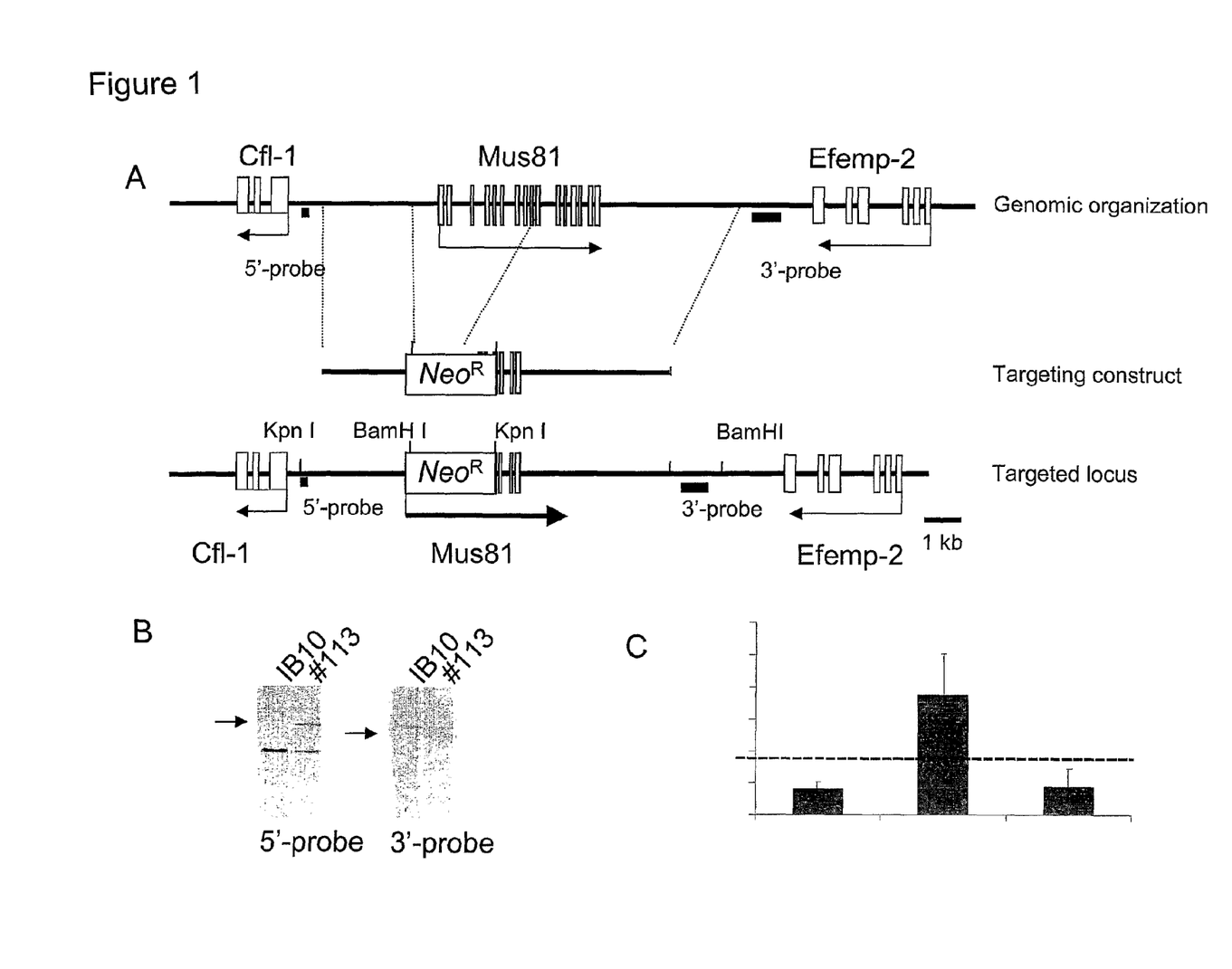
FIG. 1. (A) Generation of Mus81$^{+/-}$ ES cells. (a) Schematic representation of the Mus81 genomic locus, the gene targeting constructs and the targeted Mus81 allele. The 5' part encompassing exons 1-8 of Mus81 gene were replaced by the Tkneo selectable marker (Neo$^R$). (B) Southern blot analysis of wild-type (IB10) and targeted (#113) ES cell clones. DNA was digested with KpnI and probed with the indicated 5' probe or digested with HindIII and probed with the indicated 3' probe. (C) Expression levels of Efemp2, Cof1 and Mus81 in the aorta WT and Mus81 knockout mice. Indicated are the percentage (%) of relative mRNA expression levels of Efemp2, Mus81 and Cfl1 in the aortas of Mus81$^{-/-}$ mice as compared to wt littermate controls. Dotted line indicates the 100% (no change).

The fibulins are a family of proteins that are associated with basement membranes and elastic extracellular matrix fibres. The fibulins are minimally defined as having a series of epidermal growth factor (EGF)-like modules, followed by a carboxy-terminal fibulin-type module (FIG. 1). The fibulins are an ancient family of proteins, which are highly conserved in species as evolutionarily distant as worms and humans. Fibulins have a diverse array of protein ligands (Timpl et al. Nature Rev. Mol. Cell Biol., 4, 479-489). As a consequence of these widespread interactions, fibulins are hypothesized to function as intramolecular bridges that stabilize the organization of supramolecular ECM structures, such as elastic fibres and basement membranes.

Fibulins are prominently expressed in blood vessels. Fibulins 1 and 2 are highly expressed during cardiac valvuloseptal formation. Both are produced by migratory cardiac mesenchymal cells that have transdifferentiated from endocardial cells (Bouchey et al., 1996; Tsuda et al., 2001; Zhang et al., 1995). Fibulin 4 is found in the medial layers of large veins and arteries and in some small capillaries (Giltay et al., 1999). In developing and adult heart valves, fibulins 1 and 2 are prominently expressed and fibulin 4 is moderately expressed (Giltay et al., 1999; Zhang et al., 1995).

The importance of the fibulins in development and disease has been highlighted by gene-targeting experiments in animal models and the identification of spontaneous mutations in humans. For a review on the role of fibulins in physiology and disease see Argraves et al. (EMBO Rep. 2003 December; 4(12):1127-31) and references cited therein. For example, fibulin-1 deficiency in mice causes extensive haemorrhaging and perinatal death. Knockout experiments emphasize the essential role that fibulin-5 has in elastic fibre assembly (Yanagisawa et al. Nature 2002, Vol. 415; 168-171). Nakamura et al. Nature 2002, Vol. 415; 171-175). Mice deficient in the expression of fibulin-5, an elastin-binding protein, are viable but show symptoms of defective elastic fibre formation, including a tortuous aorta, severe emphysema and loose skin (cutis laxa). Despite the disorganized elastic lamina, there was no indication of aneurysms or of dissections of the medial layers of aortae in fibulin-5-deficient mice (Yanagisawa et al. Nature 2002, Vol. 415; 168-171). Hearts of Fibulin-5$^{-/-}$ mice of Nakamura et al. showed variable severity of right ventricular enlargement and right-sided heart failure.

The physiological role of Fibulin-4, which is most closely related to Fibulin-5 (see FIG. 1), was heretofore never established in an animal knock-out model. The phenotype of mice with decreased Fibulin-4 expression with respect to cardiovascular defects (see Experimental section below) was clearly distinct from and unexpected on the basis of the reported phenotype of Fibulin-5 deficient animals.

In another aspect, the invention relates to a method for providing an animal model for cardiovascular disease. The standard methods of genetic engineering that are available for introducing the disruption of the Fibulin-4 gene include homologous recombination, viral vector gene trapping, irradiation, chemical mutagenesis, and the transgenic expression of a nucleotide sequence encoding antisense RNA alone or in combination with catalytic ribozymes. Preferred methods for genetic modification to disrupt a Fibulin-4 gene are those, which modify an endogenous gene by inserting a "foreign nucleic acid sequence" into the gene locus, e.g., by homologous recombination or viral vector gene trapping. A "foreign nucleic acid sequence" is an exogenous sequence that is non-naturally occurring in the gene. This insertion of foreign DNA can occur within any region of the Fibulin-4 gene.

By a Fibulin-4 gene that is "disrupted" is meant a Fibulin-4 gene that is genetically modified such that the cellular activity of the Fibulin-4 polypeptide encoded by the disrupted gene is decreased or eliminated in cells that normally express a wild type version of the Fibulin-4 gene. This reduction in Fibulin-4 polypeptide activity results from either reduced Fibulin-4 gene expression (i.e. Fibulin-4 mRNA levels are effectively reduced, resulting in reduced levels of Fibulin-4 polypeptide) and/or because the disrupted Fibulin-4 gene encodes a mutated polypeptide with altered, e.g., reduced, function or stability as compared to a wild type Fibulin-4 polypeptide. Preferably, the activity of Fibulin-4 polypeptide in the genetically-modified, non-human mammal is reduced to 50% or less of wild type levels, more preferably, to 25% or less, and, even more preferably, to 10% or less of wild type levels. In one preferred embodiment, the Fibulin-4 gene disruption results in non-detectable Fibulin-4 protein levels in aortic tissue as assessed by known methodologies.

The Fibulin-4 gene locus can be disrupted by one of the several techniques for genetic modification known in the art, including chemical mutagenesis (Rinchik, Trends in Genetics 7: 15-21, 1991, Russell, Environmental & Molecular Mutagenesis 23 (Suppl. 24): 23-29, 1994), irradiation (Russell, supra), transgenic expression of Fibulin-4 gene antisense RNA, either alone or in combination with a catalytic RNA ribozyme sequence (Luyckx et al., Proc. Natl. Acad. Sci. 96: 12174-79, 1999; Sokol et al., Transgenic Research 5: 363-71, 1996; Efrat et al., Proc. Natl. Acad. Sci. USA 91: 2051-55, 1994; Larsson et al., Nucleic Acids Research 22: 2242-48, 1994) and the disruption of the Fibulin-4 gene by the insertion of a foreign nucleic acid sequence into the Fibulin-4 gene locus. Preferably, the foreign sequence is inserted by homologous recombination or by the insertion of a viral vector.

The integration of the foreign sequence disrupts the Fibulin-4 gene through one or more of the following mechanisms: by interfering with the Fibulin-4 gene transcription or translation process (e.g., by interfering with promoter recognition, or by introducing a transcription termination site or a translational stop codon into the Fibulin-4 gene); or by distorting the Fibulin-4 gene coding sequence such that it no longer encodes a Fibulin-4 polypeptide with normal function (e.g., by inserting a foreign coding sequence into the Fibulin-4 gene coding sequence, by introducing a frameshift mutation or amino acid (s) substitution, or, in the case of a double crossover event, by deleting a portion of the Fibulin-4 gene coding sequence that is required for expression of a functional Fibulin-4 protein).

To insert a foreign sequence into a Fibulin-4 gene locus in the genome of a cell to create the genetically modified non-human mammal of the invention, the foreign DNA sequence is introduced into the cell according to a standard method known in the art such as electroporation, calcium-phosphate precipitation, retroviral infection, microinjection, liposome transfection, DEAE-dextran transfection, or transferrinfection (see, e.g., Neumann et al., EMBO J. 1: 841-845, 1982; Potter et al., Proc. Natl. Acad. Sci USA 81: 7161-65, 1984; Chu et al., Nucleic Acids Res. 15: 1311-26, 1987; Thomas and Capecchi, Cell 51: 503-12, 1987; Baum et al., Biotechniques 17: 1058-62, 1994; Biewenga et al., J. Neuroscience Methods 71: 67-75, 1997; Zhang et al., Biotechniques 15: 868-72, 1993; Ray and Gage, Biotechniques 13: 598-603, 1992; Lo, Mol. Cell. Biol. 3: 1803-14, 1983; Nickoloff et al., Mol. Biotech. 10: 93-101, 1998; Linney et al., Dev. Biol. (Orlando) 213: 207-16, 1999; Zimmer and Gruss, Nature 338: 150-153, 1989; and Robertson et al., Nature 323: 445-48, 1986).

In one embodiment, homologous recombination is used to disrupt the Fibulin-4 gene. The method of homologous recombination targets the Fibulin-4 gene for disruption by introducing a Fibulin-4 gene targeting vector into a cell containing a Fibulin-4 gene. The ability of the vector to target the Fibulin-4 gene for disruption stems from using a nucleotide sequence in the vector that is homologous, i.e. related, to the Fibulin-4 gene. This homology region facilitates hybridization between the vector and the endogenous sequence of the Fibulin-4 gene. Upon hybridization, the probability of a crossover event between the targeting vector and genomic sequences greatly increases. This crossover event results in the integration of the vector sequence into the Fibulin-4 gene locus and the functional disruption of the Fibulin-4 gene.

General principles regarding the construction of vectors used for targeting are reviewed in Bradley et al. (Biotechnol. 10: 534, 1992). Two different types of vector can be used to insert DNA by homologous recombination: an insertion vector or a replacement vector. An insertion vector is circular DNA, which contains a region of Fibulin-4 gene homology with a double stranded break. Following hybridization between the homology region and the endogenous Fibulin-4 gene, a single crossover event at the double stranded break results in the insertion of the entire vector sequence into the endogenous gene at the site of crossover. A replacement vector contains two regions of homology with the Fibulin-4 gene with a non-homologous region in between. This results in the replacement of the section between the homologous regions from the gene by the corresponding section of the vector.

By a "genetically-modified, non-human mammal" containing a disrupted Fibulin-4 gene is meant a non-human mammal that is originally produced, for example, by creating a blastocyst or embryo carrying the desired genetic modification and then implanting the blastocyst or embryo in a foster mother for in utero development. The genetically-modified blastocyst or embryo can be made, in the case of mice, by implanting a genetically-modified embryonic stem (ES) cell into a mouse blastocyst or by aggregating ES cells with tetraploid embryos. In another method chimeric animals may be created by aggregation using ES cells and morula stage (8 cell) embryos (diploid). Alternatively, various species of genetically-modified embryos can be obtained by nuclear transfer. In the case of nuclear transfer, the donor cell is a somatic cell or a pluripotent stem cell, and it is engineered to contain the desired genetic modification that disrupts the Fibulin-4 gene. The nucleus of this cell is then transferred into a fertilized or parthenogenetic oocyte that is enucleated; the resultant embryo is reconstituted and developed into a blastocyst. A genetically-modified blastocyst produced by either of the above methods is then implanted into a foster mother according to standard methods well known to those skilled in the art.

A "genetically-modified, non-human mammal" includes all progeny of the non-human mammals created by the methods described above, provided that the progeny inherit at least one copy of the genetic modification that disrupts the Fibulin-4 gene. It is preferred that all somatic cells and germline cells of the genetically-modified mammal contain the modification. Preferred mammals that are genetically-modified to contain a disrupted Fibulin-4 gene include cats, dogs, sheep, pigs and rodents, such as mice, rats, rabbits, guinea pigs, hamsters and ferrets.

Also provided herein is a genetically-modified animal cell containing a disrupted Fibulin-4 gene, i.e. an animal cell, including a human cell, created by genetic engineering to contain a disrupted Fibulin-4 gene, as well as daughter cells that inherit the disrupted Fibulin-4 gene. These cells may be genetically-modified in culture according to any standard method known in the art. As an alternative to genetically modifying the cells in culture, mammalian cells may also be isolated from a genetically-modified mammal that contains a Fibulin-4 gene disruption. The animal cells of the invention may be obtained from primary cell or tissue preparations as well as culture-adapted, tumorigenic, or transformed cell lines. These cells and cell lines are derived, for example, from endothelial cells, epithelial cells, islets, neurons and other neural tissue-derived cells, mesothelial cells, osteocytes, lymphocytes, chondrocytes, hematopoietic cells, immune cells, cells of the major glands or organs (e.g., testicle, liver, lung, heart, stomach, pancreas, kidney, and skin), muscle cells (including cells from skeletal muscle, smooth muscle, and cardiac muscle), exocrine or endocrine cells, fibroblasts, and embryonic and other totipotent or pluripotent stemcells (e.g. ES cells, ES-like cells, and embryonic germline (EG) cells, and other stem cells, such as progenitor cells and tissue-derived stem cells). The cells from a genetically modified animal can be isolated from tissue or organs using techniques known to those of skill in the art. In one embodiment, the genetically modified cells of the invention are immortalized. In accordance with this embodiment, cells can be immortalized by genetically engineering the telomerase gene, an oncogene, e.g., mos or v-src, or an apoptosis-inhibiting gene, e.g., Bcl-2, into the cells. Alternatively, cells can be immortalized by fusion with a hybridization partner utilizing techniques known to one of skill in the art. The genetically modified animal cell containing a disrupted Fibulin-4 gene may be used for in vitro studies. For instance, Fibulin-4 deficient cells can be used to investigate biochemical and/or genetic aspects involved with the deficiency, such as (inducible) tissue collagenase or metalloproteinase expression in aortic endothelial cells. Cells with a disrupted Fibulin-4 gene can also be used in tissue engineering to provide a tissue or organ model for disease.

In a further aspect, the invention provides the use of a genetically modified cell or non-human mammal according to the invention as experimental disease model. The phenotypic characteristics of the mice are described in detail below. Briefly, pathological abnormalities of Fibulin-4 deficient mice which had suddenly died included an enlarged or dissected aorta (aneurysm), disturbed elastin conformation in aorta and an increased size of the heart (in particular the left ventricle; see FIG. 3). With respect to hemodynamic parameters, no differences were observed in heart rate and mean aortic pressure between mice that were heterozygous (+/R) or homozygous (R/R) for the Fibulin-4 gene disruption. However, R/R mice showed increased pulse pressure and aortic insuffiency (see FIG. 4).

The animal model or cell can be applied in cardiovascular research and industry for the screening, selection and validation of a drug compound, either a known drug compound or a candidate drug compound. For example, they can be used in drug development and validation procedure to identify therapeutics for the treatment of heart disease and failure (such as ACE-inhibitors, statins, beta-blockers) and therapeutics affecting aortic aneurysms, aortic insufficiency and blood pressure. Aortic insufficiency is a heart valve disease in which the aortic valve weakens or balloons, preventing the valve from closing tightly. This leads to backward flow of blood from the aorta (the largest blood vessel) into the left ventricle (the left lower chamber of the heart).

Therefore the invention relates to a method for identifying or validating a compound that can be used to treat or to prevent an aberrant cardiovascular condition, said method comprising contacting a transgenic mammal or cell according to the invention with said compound, and determining the effect of said compound on said condition, wherein detection of an improvement in said condition indicates the identification of a compound that can be used to treat or to prevent said condition.

In yet a further aspect, the invention features a method of identifying a gene that demonstrates a modified expression as a result of modified Fibulin-4 expression in an animal tissue (e.g. aortic tissue) or cell, said method comprising comparing the expression profile of a genetically modified animal tissue or cell, wherein the tissue or cell is heterozygous or homozygous for a genetic modification that disrupts the Fibulin-4 gene, preferably wherein the tissue or cell is homozygous for the disruption, to a wild type tissue cell. As is exemplified herein below, RNA expression profiles in the aorta of wild type, heterozygous and homozygous Fibulin-4 animals (non-moribund) were determined, which allowed the identification of new target genes involved in response to aortic failure. Strikingly, this approach revealed pathways implicated in the cell adhesion and extracellular matrix, blood pressure and coagulation, apoptosis and cell death and finally cell cycle regulation (FIG. 5).

The overrepresentation of cell-cell adhesion and extracellular matrix processes was evidenced by the significant upregulation of paxillin (Pxn), cadherin 11 (Cdh11), actin related protein 2/3 complex, subunit 2 (Arpc2), adhesion regulating molecule 1(Adrm1), discoidin domain receptor family, member 1(Ddr1), AE binding protein 1 (Aebp1), procollagen, type V, alpha 2 (Col5a2), integrin beta 5 (Itgb5), scavenger receptor class F, member 2 (Scarf2), moesin (Msn), ras homolog gene family, member E (Arhe), fibronectin 1(Fn1), synaptopodin (Synpo), fat tumor suppressor homolog (*Drosophila*) (Fath), stabilin 1(Stab1), syndecan 3 (Sdc3), myosin Va (Myo5a), syndecan 1(Sdc1), glycoprotein Ib, beta polypeptide (Gp1bb), procollagen, type XI, alpha 1 (Col11a1), procollagen, type VIII, alpha 1 (Col8a1), procollagen, type VIII, alpha 1 (Col8a1) and the significant down regulation of integrin alpha 8 (Itga8), sarcoglycan gamma-dystrophin-associated glycoprotein (Sgcg), actin-gamma 2-smooth muscle, enteric Actg2, dystonin Dst, and neural cell adhesion molecule 1 (Ncam1) expression levels.

With the exception of epidermal growth factor-containing fibulin-like extracellular matrix protein-2 (Efemp2) gene which, of course, due to the disruption of the gene and similarly to the Q-PCR findings (FIG. 1C), was downregulated in the aortas of Fibulin$^{R/R}$ mice as compared to the wt littermate controls, we identified a plethora of genes associated with the blood pressure and coagulation processes including the endothelin receptor type B (Ednrb), angiotensin II, type I receptor-associated protein (Agtrap), protein C receptor, endothelial (Procr), gap junction membrane channel protein alpha 4 (Gja4), prostaglandin-endoperoxide synthase 1 (Ptgs1) and glycoprotein Ib, beta polypeptide (Gp1bb), of which the expression was shown to be upregulated.

Apoptosis and cell death was evidenced at the transcriptional level (see FIG. 5), in terms of the significant upregulation of Tial1 cytotoxic granule-associated RNA binding protein-like 1 (Tial1), receptor (TNFRSF)-interacting serine-threonine kinase 2 (Ripk2), Cd27 binding protein (Hindu God of destruction, Siva-pending), tumor necrosis factor receptor superfamily, member 21 (Tnfrsf21), Bcl-associated death promoter (Bad), myeloid cell leukemia sequence 1 (Mcl1), BCL2/adenovirus E1B 19 kDa-interacting protein 1, (Bnip2), lymphotoxin B receptor (Ltbr), Bcl-2-related ovarian killer protein (Bok), chloride channel calcium activated 2 (Clca2), sulfatase 1 (Sulf1) and clusterin (Clu).

Finally, the knock-out mutation involved the upregulation of the expression of cell cycle maintenance/cell replication genes minichromosome maintenance deficient 3 (*S. cerevisiae*) (Mcm3), minichromosome maintenance deficient 4 (*S. cerevisiae*) (Mcm4) and deoxyuridine triphosphatase (Dutp) (FIG. 5).

Herewith, the invention provides the use of a genetically-modified mammal or animal cell, wherein the modification results in a disrupted Fibulin-4 gene, to identify a gene product involved in or predictive of aortic aneurysm. Accordingly, the invention relates to a method to screen for or diagnose aortic failure in a subject, preferably a human subject, said method comprising determining the level of at least one, preferably at least two, more preferably at least three, most preferred at least four, aneurysm-specific gene product(s) in a biological sample isolated from said subject, wherein said aneurysm-specific gene is involved in cell adhesion and extracellular matrix, blood pressure and coagulation, apoptosis and cell death and/or cell cycle regulation. The term "aneurysm-specific gene product" is meant to indicate that the gene product can be used as a genetic marker to indicate the chance of having or being predisposed to the development of an aneurysm. It does not exclude that the gene product is not involved in any other disease condition. Of course, the more aneurysm-specific gene products are included in the screening or diagnosis, the more reliable the outcome of the test. Preferably, said aneurysm-specific gene is at least 1.5, more preferably at least 2.00, most preferably at least 2.50-fold over- or underrepresented relative to the wild-type expression level. In particular, said aneurysm-specific gene is selected from FIG. 5. In one embodiment, it is a pro-collagen, e.g. pro-collagen type XI or type VIII. In another embodiment, said aneurysm-specific gene is a syndecan gene, e.g. syndecan 1, 3 or 4. In yet another embodiment, the screening or diagnostic method involves the detection of a gene product of a receptor or receptor-associated protein involved in blood pressure regulation and coagulation, such as the endothelin receptor type B, angiotensin II type I receptor associated protein or endothelial protein C receptor.

In another aspect, the invention provides the use of an aneursym-specific gene product selected from the group of genes listed in FIG. 5 as a diagnostic or predictive marker for aortic failure. The differential expression level of aneurysm-specific genes provides a basis for new clinically applicable tools to diagnose aortic defects, as well as to screen for patients who are at increased risk of developing an aortic aneurysm before clinical symptoms become apparent.

EXPERIMENTAL SECTION

Material and Methods

Construction of Mus81 Targeting Vectors and Fibulin-4 Transgenic Mice

A Mus81 cDNA fragment was obtained from IMAGE clone: 2937030. Genomic fragments hybridizing to the Mus81 cDNA (carboxy-terminal fragment that were made by EcoRI and NotI digest from IMAGE: 2937030 were subcloned in pBluescript II KS (+) (Stratagene). The location of the intron-exon borders was determined by DNA sequence data from Celera. A targeting vector was made by inserting a cassette with the neomycin resistance gene driven by the TK promoter in the BglII sites. E14 ES cells (subclone IB10) were cultured in BRL-conditioned medium supplemented with 1000 U/ml leukemia inhibitory factor. A 10 µg portion of the NotI and SalI linearized targeting vector was electroporated into approximately $10^7$ ES cells in 400 µl. Selection with 200 µg/ml G-418 was started 24 hours after electroporation. After 8-10 days, G418-resistant clones were isolated. Screening for homologous recombinants was performed using DNA blot analysis of KpnI-digested DNA with a 300 by 5' external probe and confirmed using DNA blot analysis of BamHI-digested DNA with 1 kb 3' external probe. One clone identified as correctly targeted waE injected into C57-BL/6 blastocysts. Chimeras identified on the basis of agouti pigmentation in the coat were backcrossed to C57-BL/6 mice and the agouti offspring were genotyped by Southern blot analysis. Heterozygous mutant progeny were intercrossed to produce the animals analyzed in this study.

Quantitative Real Time PCR Expression Analysis

Total RNA was isolated from the aorta of 4 wt, 2 Fibulin$^{+/R}$ and 2 Fibulin$^{R/R}$ 10-days-old mice using a Total RNA isolation kit (Qiagen) as described by the manufacturer. Quantitative PCR (qPCR) was performed with a DNA Engine Opticon device according to the instructions of the manufacturer (MJ Research). Primer pairs, designed to generate intron-spanning products of 180-210 bp for Efemp2, Mus81 and Cfl1 were as follows: Efemp2: 5'-GGGTTATTTGTGTCTGC-CTCG-3' and 5'-TGGTAGGAGCCAGGAAGGTT-3', for Mus81: 5'-CAAAGCCTTCCACAAACCC-3' and 5'-TCAT-AAGCAGCCAGGAGACT-3', for Cfl1: 5'-CCAGAA-GAAGTGAAGAAACGC-3' and 5'-GAAGATGAACAC-CAGGTCCT-3'. The generation of specific PCR products was confirmed by melting curve analysis (which measures product specificity by the decrease in fluorescence signal when the PCR product is denatured) and gel electrophoresis (using Roche Agarose MS for analysing small PCR products). Each primer pair was tested with a logarithmic dilution of a cDNA mix to generate a linear standard curve (crossing point (CP) plotted versus log of template concentration), which was used to calculate the primer pair efficiency ($E=10^{(-1/slope)}$). Hypoxanthine guanine phosphoribosyltransferase1 (Hprt-1) mRNA was used as an external standard. For data analysis, the second derivative maximum method was applied: $(E_{1gene\ of\ interest}^{\Delta CP(cDNA\ of\ wt\ mice-cDNA\ of\ Fibulin+/R\ or\ FibulinR/R)\ gene\ of\ interest})/(E_{hprt-1}^{\Delta CP(cDNA\ of\ wt\ mice-cDNA\ of\ Fibulin+/R\ or\ FibulinR/R)hrpt-1})$ Histological Analysis Heart, aortas and lungs of Fibulin-4$^{+/+}$, Fibulin-4$^{+/R}$ and Fibulin-4$^{R/R}$ were isolated and fixed in 4% buffered formaline. After fixation macroscopical images were taken using the stereoscope, aortas were paraffin embedded and 4 µm sections were stained with Verhoeff-van Gieson stain for elastic tissue.

Echocardiography, Hemodynamic Measurements and Data Analysis

Mice (15-20 weeks old) were weighed, anesthetized with isoflurane and intubated using a 24 G intravenous catheter with a blunt end. Mice were artificially ventilated with a mixture of $O_2$ and $N_2O$ (1:2, vol/vol) to which isoflurane (2.5-3.0%, vol/vol) was added at a rate of 80 strokes/min using a rodent ventilator (SAR-830/P; CWE, Ardmore, Pa.) at 18 cm H$_2$O inspiratory pressure. The mouse was placed on a heating pad to maintain body temperature at 37° C. The chest was dehaired using Veet hair removal (Reckitt Benckiser Inc., Parsippany, N.J.). Echocardiograms were obtained with the Aloka SSD 4000 echo device (Aloka Company, Tokyo, Japan) using a 12-MHz probe. Images of the short and long axis were obtained in 2D- and M-mode settings with simultaneous ECG gating as described before (5, 12).

Following echocardiography, mice were instrumented for hemodynamic measurements. For this purpose, a polyethylene catheter (PE-10) was inserted into the left carotid artery and advanced into the aortic arch to measure aortic blood pressure. A 1.4 F microtipped manometer (Millar Instruments, Houston, Tex.; calibrated prior to each experiment with a mercury manometer) was inserted via the right carotid artery and advanced into the LV lumen to measure LV pressure and its first derivative, LV dP/dt. Subsequently, baseline recordings were obtained of aortic blood pressure, heart rate and LV pressure. Echocardiography data were stored for offline analysis. LV diameters at end-diastole (ED) and end-systole (ES) were measured from the M-mode images using Sigmascan Pro 5.0 Image Analysis software (SPSS Inc., Chigago, Ill.). Consecutive beats were analyzed by a blinded observer. LV absolute shortening (ED−ES) and fractional shortening [(ED−ES)/ED×100%] were calculated. Hemodynamic data were recorded and digitized (sampling rate 5000 sec-1 per channel) using an online four-channel data acquisition program (ATCODAS; Dataq Instruments, Akron, Ohio) for post-acquisition offline analysis with a program written in MATLAB (Mathworks, Natick, Mass.). Ten consecutive beats were selected for determination of heart rate (HR), LV peak systolic (LVSP) and end-diastolic pressures (LVEDP), diastolic aortic pressure (DAP) and the maximum rates of rise (LVdP/dtmax) and fall (LVdP/dtmin) of LV pressure as well as the rate of rise of LV pressure at a pressure of 30 mmHg (LVdP/dtP30). In addition the time constant of LV pressure decay ô, an index of early LV relaxation, was computed as described earlier (5, 13). Pressure-diameter relations were constructed with a program written in MATLAB, using the ECG signal for synchronization of the echocardiography M-mode dataset and the LV pressure signal. Data from four consecutive beats were averaged.

Micro Array Hybridizations

Standard procedures were used to obtain total RNA (Qiagen) from the aorta of 4 wt, 2 Fibulin$^{+/R}$ and 2 Fibulin$^{R/R}$ 10-days-old mice. Synthesis of double stranded cDNA and biotin labeled cRNA was performed according to the instructions of the manufacturer (Affymetrix). Fragmented cRNA preparations were hybridized to full mouse genome oligonucleotide arrays (Affymetrix, mouse expression 430 V2.0 arrays), using a hybridization Oven 640 (Affymetrix), washed, and subsequently scanned on a GeneChip Scanner 3000 (Affymetrix). Initial data extraction and normalization within each array was performed by means of the GCOS software (Affymetrix). Data intensities were Log transformed and normalized within and between arrays by means of the quantile normalization method as previously described (11). One-way analysis of variance (ANOVA) was employed by means of the Spotfire Decision Site software package 7.2 v10.0 (Spotfire Inc., MA, USA) to extract the statistically significant data from each of the four individual microarrays obtained for each genotype. The criteria for significance were set at $p \leq 0.01$ and a positive or negative 1.5-fold change.

Gene Ontology Classification and Network Analysis

All significant gene entries were subjected to GO classification (http://www.geneontology.org). Significant over-representation of GO-classified biological processes was assessed by comparing the number of pertinent genes in a given biological process to the total number of the relevant genes printed on the array for that particular biological process (Fisher exact test, $P \leq 0.05$, False detection rate (FDR) $\leq 0.1$) using the publicly accessible software Ease (4). Network data were generated through the use of Ingenuity Pathways Analysis (www.ingenuity.com), a web-delivered application that enables biologists to discover, visualize and explore therapeutically relevant networks significant to their experimental results, such as gene expression array data sets. GO-classified significant data and network analysis results can be visualized in a highly interactive manner Results Targeted Integration of the Tkneo Gene in the Mus81 Locus Results in Decreased Expression of Fibulin-4

FIG. 1 shows part of the chromosomal organization of mouse chromosome 19 encompassing the cofilin (CFL-1), Mus81 and the fibulin-4 (efemp2, FBLN-4) genes. We initially designed a targeting construct to disrupt the Mus81 gene. The Mus81-EmeI endonuclease is implicated in the rescue of broken replication forks in yeast. Mus81 knockout mice have been developed before by other groups (2, 8). In the targeting strategy of Dendouda et al, exons 9-12 were replaced by PGK-Neo marker flanked by pLox sites and subsequently the marker was excised in mice using Cre-recombinase expressing mice. Mus81 knockout mice from which the selectable marker was removed were born at expected Mendelian frequencies and were indistinguishable from wild-type littermates in terms of development, growth, immune function and fertility (2). In our targeting strategy, proper integration of the Mus81 targeting construct replaces exon 1-8 of the Mus81 gene by the Tkneo expression cassette. The transcription orientation of the TK-neo gene is indicated with an arrow. Transcription of the Fibulin-4 gene, also indicated with an arrow is opposite to the transcription of the TKneo gene, possibly resulting in transcriptional interference, resulting in downregulation of the expression of the Fibulin-4 gene. Southern analysis of 200 candidate clones yielded one homologously targeted integration of the Tkneo gene in the Mus81 locus, that showed proper integration with 3' and 5' probes (FIG. 1B).

Next we sought to examine whether Tkneo integration altered significantly the transcriptional activity of neighboring genes, as has been previously observed (10). To this end, we determined the expression levels of Efemp2, Mus81 and Cfl1 genes by means of Q-PCR in the aortas of wt and Fibulin-$4^{R/R-}$ 1—days-old mice. Here, we evidenced a substantial decrease in the expression levels of Efemp2/Fibulin-4 and Mus81 genes. Importantly, however, Cfl1 gene was upregulated as compared to wt littermate controls (FIG. 1C). Since Cfl1 is expressed in opposite direction to the TKneo marker, our findings are in agreement with the previously predicted Tkneo transcriptional interference.

Embryonic Viability and Life-Span of Fibulin-R$^{R/+}$ and Fibulin-4$^{R/R}$ Mice.

Figure 2:
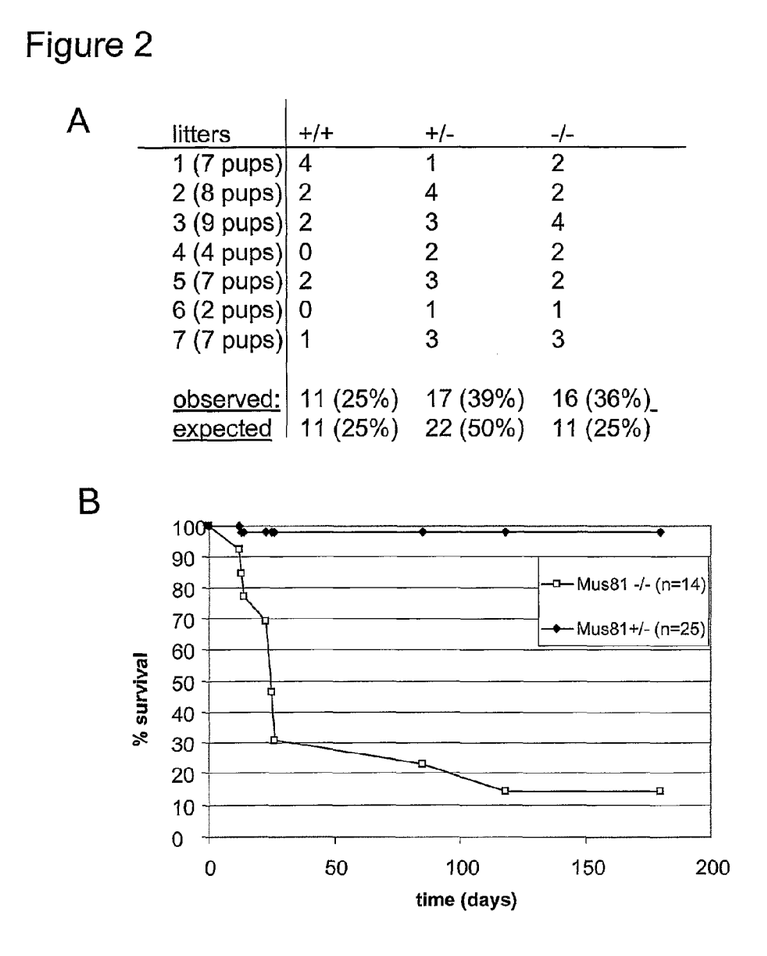
FIG. 2. (A) Fibulin$^{R/R}$ mice are born at expected Mendelian frequencies. Indicated are the genotypes found after crossing Fibulin$^{+/R}$ X Fibulin$^{+/R}$ mice. (B) Survival of Fibulin$^{+/R}$ and Fibulin$^{R/R}$ mice after birth.

As both Fibulin-4$^{R/+}$ and Fibulin-4$^{R/R}$ are born at expected Mendelian frequencies and exhibited no gross phenotypic abnormalities at birth, decreased expression of Fibulin-4 does not appear to impair embryonic viability (FIG. 2A). Up to 2 weeks of age, heterozygous Fibulin-4$^{+/R}$ that express 2-fold less levels of Fibulin-4 and Fibulin-4$^{R/R}$ that express 4-fold less levels of Fibulin-4 are morphologically indistinguishable from wild-type littermates. However, up to 80% of the Fibulin-4$^{R/R}$ mice suddenly die of cardiovascular complications before reaching weaning age (approximately two to three weeks after births). Within this group of 20% remaining Fibulin-4$^{R/R}$ surviving mice, sudden death was sporadically observed after the mice reached the age of 2 weeks. Surviving Fibulin-4$^{R/R}$ mice do not show gross abnormalities and are indistinguishable from wild-type or heterozygous littermates. Necroscopy was performed on two homozygous mutant animals that had died naturally at 9 or 10 days of age. Both showed evidence of vascular compromise with haemopericardium causing cardiac tamponade. Serial sectioning of the aorta of one of these mice showed an aortic dissection of the ascending aorta (data not shown).

Pathology

Figure 3:
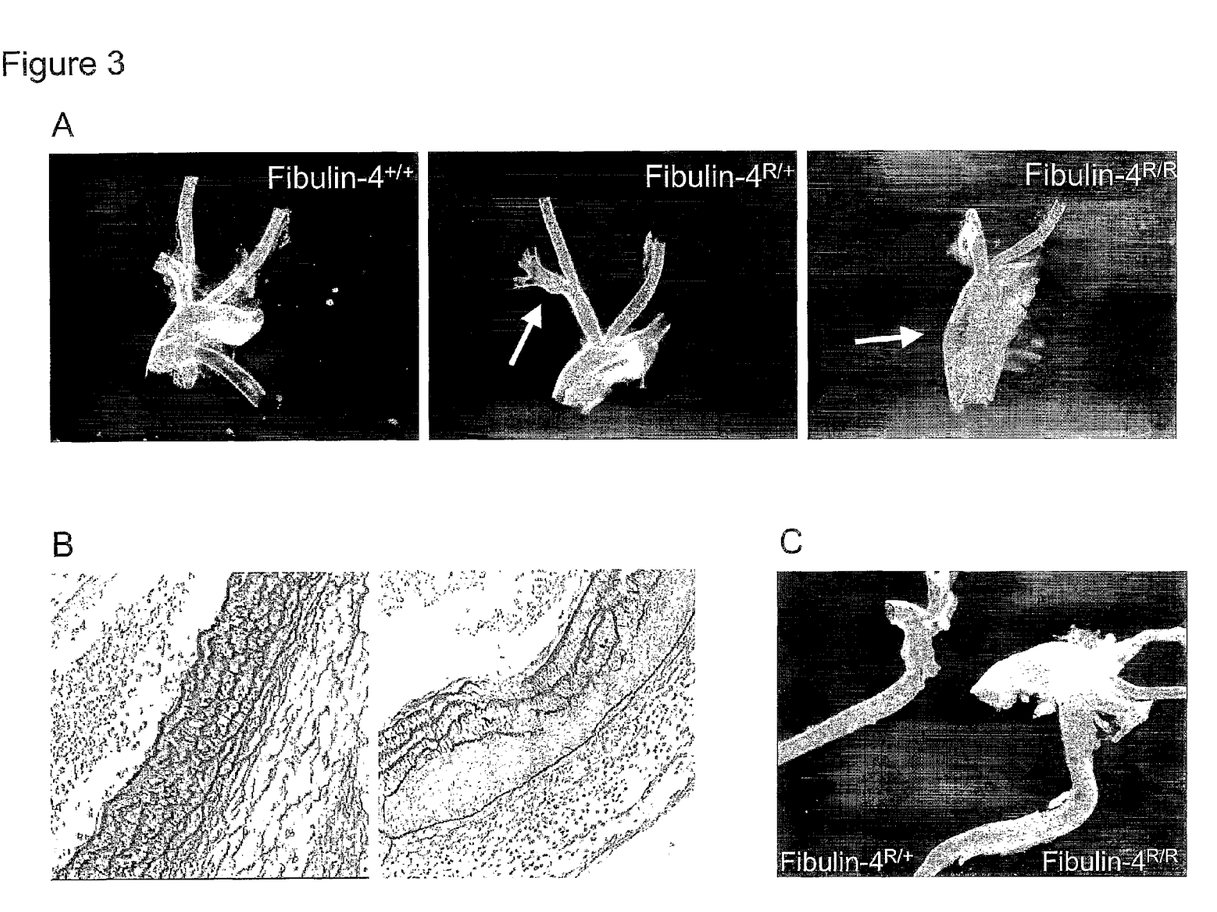
FIG. 3. (A) Morphology of the aorta of new-born wild-type (left panel), Fibulin-4$^{R/+}$ (center panel) and Fibulin-4$^{R/R}$ (right panel) mice. (B) Elastin staining of longitudinal sections of the ascending aorta of Fibulin-4$^{R/R}$ mice with regions with well-organized elastic laminae (left) en regions with affected laminae (right). (C) Macroscopic abnormalities of the aorta of 15-week old survivor Fibulin-4$^{R/R}$ mice. For comparison, a similar biopsy of a heterozygous mouse is shown.

We compared the morphology of the aorta of newborn wild-type, Fibulin-4$^{R/+}$ and Fibulin-4$^{R/R}$ mice (left, center and right panel of FIG. 3A, respectively). Newborn (p18) Fibulin-4$^{R/+}$ showed abnormal ballooning of the innominate artery/brachiocephalic trunk, indicative for aneurysm. Newborn Fibulin-4$^{R/R}$ mice showed dramatic dilatation of the ascencing aorta resulting in an aorta with an at least 2-fold enlarged diameter. Two week old Fibulin-4$^{R/R}$ mice showed similar aortic dilatation and an increased heart size due to an enlarged right ventricle.

To investigate the underlying defect that caused the aortic abnormalities in Fibulin-4$^{R/R}$ mice, we performed histological examinations of aortas from these mice. Elastin staining of longitudinal sections of the ascending aorta of Fibulin-4$^{R/R}$ mice showed regions with well-organized elastic laminae (FIG. 3B, left), but also region with dramatically affected laminae (FIG. 3B, right). The regions with severely disorganized and fragmented laminae also showed signs of leakage of blood through the laminae layers.

In addition, disruption of the elastic laminae was already evident as early as postnatal day 1. This indicated that the defect seen in adult aortas of homozygous mice was not a result of degradation of intact elastic laminae by activated inflammatory cells, but rather the consequence of an underlying developmental defect in the final organization of the elastic fibers in Fibulin-4$^{R/R}$ mice.

We also analyzed 15-week-old Fibulin-4$^{R/R}$ mice from the "survivors" (FIG. 3C). Although they show no differences in gross appearance compared to their heterozygous and wild-type littermates, aortas of these Fibulin-4$^{R/R}$ mice showed clear macroscopic abnormalities. They had severely enlarged aortas, showing hyperplasia with accumulation of excessive collagen and signs of bleeding.

Hemodynamic Measurements

Figure 4:
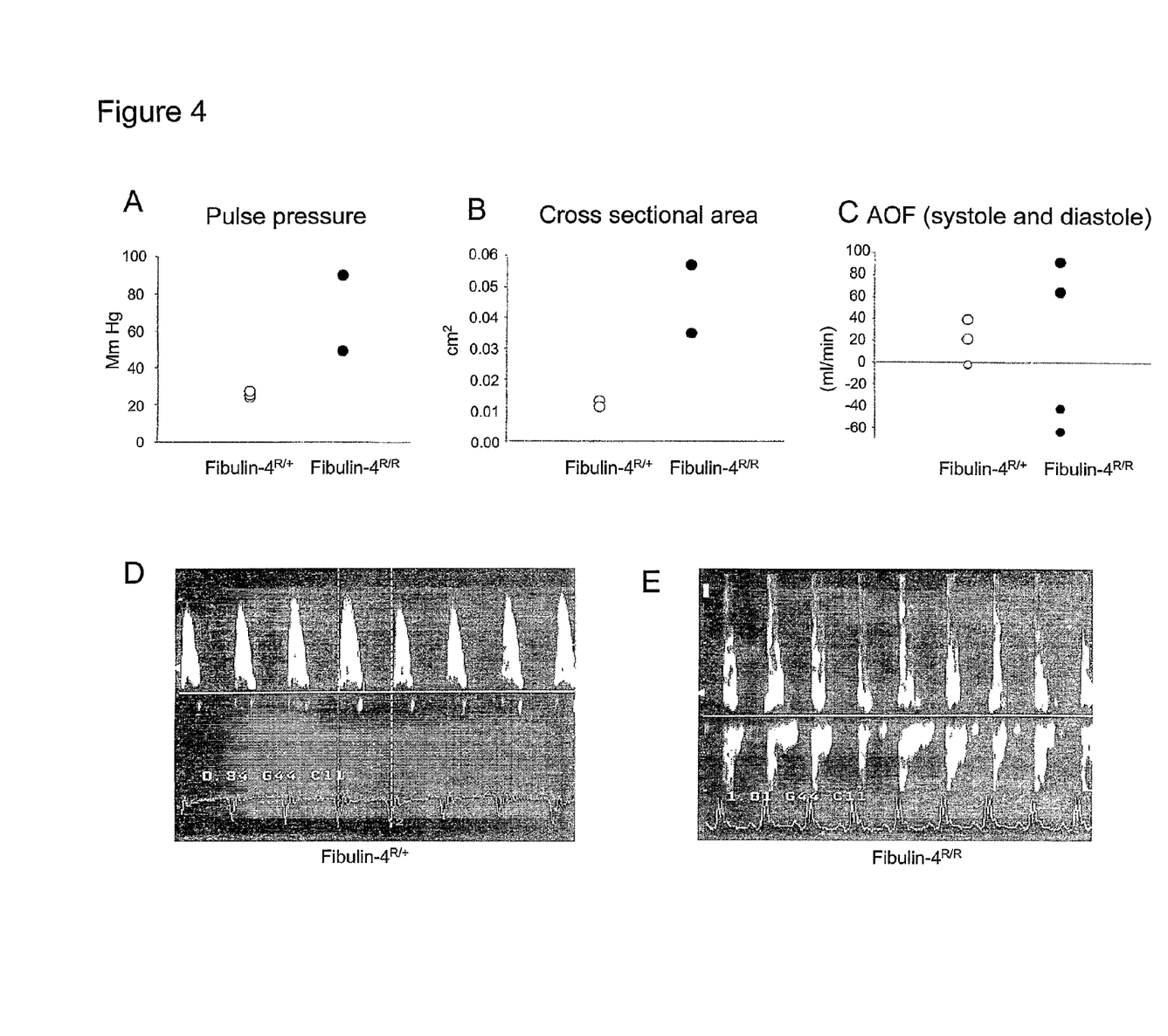
FIG. 4. Hemodynamic parameters in Fibulin-4$^{R/+}$ and Fibulin-4$^{R/R}$ mice. Panel A: Aortic pulse pressure in mm Hg. Panel B: Cross sectional area of aorta. Panel C: aortic blood flow (AOF). Panels D and E: Echo pictures of aorta of Fibulin-4$^{+/R}$ (panel D) and Fibulin-4$^{R/R}$ (panel E) mice.

No differences were observed in the various groups of mice with respect to heart rate, mean aortic pressure, fractional shortening, $-dP/dt_{P30}$. Fibulin-4 deficient mice showed slight increases in diameter ED (end-diastole), ES (end-systole), and wall thickness ED and ES. Significant increases were observed in the deficient mice with respect to the left ventricle weight (LVW). The LVW/BW (=bodyweight) observed in heterozygous Fibulin-4$^{+/R}$ mice was 3-4 mg/g, as is typically observed for wild-type mice, whereas in homozygous Fibulin-4$^{R/R}$ mice it was 4-8 mg/g. Furthermore, Fibulin-4 deficient mice displayed an increased aortic pulse pressure, which is defined as the systolic pressure minus the diastolic pressure (FIG. 4A). Interestingly, the cross sectional area of the aorta was found to be minimally 2-fold increased in mice that are homozygous for the Fibulin-4 gene disruption as compared to heterozygous mice (FIG. 4B).

As indicated by FIG. 4C, the AOF (aortic blood flow) measurements showed an increased systolic flow and a decreased diastolic flow (negative values) in Fibulin-4$^{R/R}$ mice, which is indicative for aortic insufficiency. However, resulting mean, AOF is similar in Fibulin$^{R/+}$ and Fibulin$^{R/R}$ mice and comparable to values reported for wild-type mice.

FIGS. 4D and 4E show echo pictures of Fibulin-4$^{+/R}$ and Fibulin-4$^{R/R}$ aortas, demonstrating a showing severe aortic insufficiency (backflow) in Fibulin-4$^{R/R}$ mice.

Analysis of the Mus81$^{-/-}$ Mouse Aorta Transcriptome

In order to obtain an unbiased insight into the severe phenotype of Fibulin-4$^{R/R}$ mouse, we scanned the full mouse genome expression profiles of 4 wt, 2 Fibulin$^{+/R}$ and 2 Fibulin$^{R/R}$ (non-moribund) 10-days-old mice. One-way analysis of variance (ANOVA) of Affymetrix full mouse genome arrays revealed 549 probe sets describing 464 unique genes that changed significantly between the different genotypes (p<0.01, ±1.2 fold change); this number is significantly greater than the 20 genes that are expected to occur due to random change alone under these selection criteria. An initial, unbiased analysis identified those biological processes containing a significantly disproportionate number of genes relative to those printed on the microarrays and were flagged as 'over-represented'. Strikingly, this approach revealed pathways implicated in the cell adhesion and extracellular matrix, blood pressure and coagulation, apoptosis and cell death and finally cell cycle regulation (FIG. 5).

REFERENCES

1. Argraves, W. S., L. M. Greene, M. A. Cooley, and W. M. Gallagher. 2003. Fibulins: physiological and disease perspectives. EMBO Rep 4:1127-31.
2. Dendouga, N., H. Gao, D. Moechars, M. Janicot, J. Vialard, and C. H. McGowan. 2005. Disruption of murine Mus81 increase genomic instability and DNA damage sensitivity but does not promote tumorigenesis. Mol. Cell. Biol in press.
3. Giltay, R., R. Timpl, and G. Kostka. 1999. Sequence, recombinant expression and tissue localization of two novel extracellular matrix proteins, fibulin-3 and fibulin-4. Matrix Biol 18:469-80.
4. Hosack, D. A., G. Dennis, Jr., B. T. Sherman, H. C. Lane, and R. A. Lempicki. 2003. Identifying biological themes within lists of genes with EASE. Genome Biol 4:R70.
5. Kamphoven, J. H., R. Stubenitsky, A. J. Reuser, A. T. Van Der Ploeg, P. D. Verdouw, and D. J. Duncker. 2001. Cardiac remodeling and contractile function in acid alpha-glucosidase knockout mice. Physiol Genomics 5:171-9.
6. Kostka, G., R. Giltay, W. Bloch, K. Addicks, R. Timpl, R Fassler, and M. L. Chu. 2001. Perinatal lethality and endothelial cell abnormalities in several vessel compartments of fibulin-1-deficient mice. Mol Cell Biol 21:7025-34.
7. Loeys, B., L. Van Maldergem, G. Mortier, P. Coucke, S. Gerniers, J. M. Naeyaert, and A. De Paepe. 2002. Homozygosity for a missense mutation in fibulin-5 (FBLN5) results in a severe form of cutis laxa. Hum Mol Genet 11:2113-8.
8. McPherson, J. P., B. Lemmers, R. Chahwan, A. Pamidi, E. Migon, E. Matysiak-Zablocki, M. E. Moynahan, J. Essers, K. Hanada, A. Poonepalli, O. Sanchez-Sweatman, R. Khokha, R. Kanaar, M. Jasin, M. P. Hande, and R. Hakem. 2004. Involvement of mammalian Mus81 in genome integrity and tumor suppression. Science 304:1822-6.
9. Nakamura, T., P. R. Lozano, Y. Ikeda, Y. Iwanaga, A. Hinek, S. Minamisawa, C. F. Cheng, K. Kobuke, N. Dalton, Y. Takada, K. Tashiro, J. Ross Jr, T. Honjo, and K. R. Chien. 2002. Fibulin-5/DANCE is essential for elastogenesis in vivo. Nature 415:171-5.
10. Olson, E. N., H. H. Arnold, P. W. Rigby, and B. J. Wold. 1996. Know your neighbors: three phenotypes in null mutants of the myogenic bHLH gene MRF4. Cell 85:1-4.
11. Peeters, P. J., F. L. Fierens, I. van den Wyngaert, H. W. Goehlmann, S. M. Swagemakers, S. U. Kass, X. Langlois, S. Pullan, M. P. Stenzel-Poore, and T. Steckler. 2004. Gene expression profiles highlight adaptive brain mechanisms in corticotropin releasing factor overexpressing mice. Brain Res Mol Brain Res 129:135-50.

12. Tanaka, N., N. Dalton, L. Mao, H. A. Rockman, K. L. Peterson, K. R. Gottshall, J. J. Hunter, K. R. Chien, and J. Ross, Jr. 1996. Transthoracic echocardiography in models of cardiac disease in the mouse. Circulation 94:1109-17.

13. van der Velden, J., D. Merkus, B. R. Klarenbeek, A. T. James, N. M. Boontje, D. H. Dekkers, G. J. Stienen, J. M. Lamers, and D. J. Duncker. 2004. Alterations in myofilament function contribute to left ventricular dysfunction in pigs early after myocardial infarction. Circ Res 95:e85-95.

14. Yanagisawa, H., E. C. Davis, B. C. Starcher, T. Ouchi, M. Yanagisawa, J. A. Richardson, and E. N. Olson. 2002. Fibulin-5 is an elastin-binding protein essential for elastic fibre development in vivo. Nature 415:168-71.

The invention claimed is:

1. A genetically-modified mouse whose genome comprises a disrupted Fibulin-4 gene, wherein the mouse exhibits aortic aneurysm, aortic insufficiency or hypertension.

2. The mouse according to claim 1, exhibiting at least a 2-fold reduction in Fibulin-4 RNA expression in aortic tissue when compared to a wild-type animal mouse.

3. The mouse, according to claim 2, wherein the mammal mouse is heterozygous for disruption of the Fibulin-4 gene.

4. The mouse according to claim 2, wherein the mammal mouse is homozygous for disruption of the Fibulin-4 gene.

5. The mouse according to claim 1, wherein the mouse is heterozygous for disruption of the Fibulin-4 gene.

6. The mouse according to claim 1, wherein the mouse is homozygous for disruption of the Fibulin-4 gene.

7. The mouse according to claim 1, wherein the mouse can be used to identify a gene product involved in or predictive of aortic aneurysm.

8. An isolated genetically-modified animal mouse cell containing a disrupted Fibulin-4 gene.

9. A model for a cardiovascular condition or disease, wherein the model is a genetically-modified mouse whose genome comprises a disrupted Fibulin-4 gene, wherein the mouse exhibits aortic aneurysm, aortic insufficiency or hypertension.

10. The model according to claim 9, wherein the cardiovascular condition is a thoracic aortic aneurysm.

11. A method for identifying or validating a compound that can be used to treat or to prevent a cardiovascular condition, said method comprising the steps of contacting a genetically-modified mouse whose genome comprises a disrupted Fibulin-4 gene, wherein the mouse exhibits aortic aneurysm, aortic insufficiency or hypertension with a compound, and determining the effect of said compound on said condition, wherein detection of an improvement in said condition indicates the identification of a compound that can be used to -eat or to prevent said condition.

12. The method according to claim 11, wherein said mouse is homozygous for a disruption in the gene encoding Fibulin-4.

13. The method according to claim 11, wherein said condition is aortic aneurysm, aortic insufficiency or hypertension.

* * * * *

UNITED STATES PATENT AND TRADEMARK OFFICE
CERTIFICATE OF CORRECTION

PATENT NO. : 8,420,886 B2  
APPLICATION NO. : 11/996392  
DATED : April 16, 2013  
INVENTOR(S) : Jeroen Essers et al.

Page 1 of 1

It is certified that error appears in the above-identified patent and that said Letters Patent is hereby corrected as shown below:

On the Title Page, Item (56), Column 2, Other Publications, line 5, "208-216.")"
should read -- 208-216. --

In the Claims:

Column 17, Line 18, Claim 2, after "wild-type" delete "animal"

Column 17, Line 19, Claim 3, after "mouse" delete ","

Column 17, Line 19, Claim 3, after "the" delete "mammal"

Column 17, Line 21, Claim 4, after "the" delete "mammal"

Column 17, Line 30, Claim 8, after "modified" delete "animal"

Column 18, Line 25, Claim 11, delete "-eat" and insert -- treat --

Signed and Sealed this  
Sixteenth Day of July, 2013

Teresa Stanek Rea  
*Acting Director of the United States Patent and Trademark Office*

UNITED STATES PATENT AND TRADEMARK OFFICE
CERTIFICATE OF CORRECTION

PATENT NO. : 8,420,886 B2
APPLICATION NO. : 11/996392
DATED : April 16, 2013
INVENTOR(S) : Essers et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1421 days.

Signed and Sealed this
Eighth Day of September, 2015

Michelle K. Lee
*Director of the United States Patent and Trademark Office*